United States Patent
Eriksson et al.

(10) Patent No.: US 9,907,867 B2
(45) Date of Patent: Mar. 6, 2018

(54) SYSTEMS, METHODS AND APPARATUS FOR MANUFACTURING RADIOISOTOPES

(71) Applicant: GENERAL ELECTRIC COMPANY, Schenectady, NY (US)

(72) Inventors: Tomas Eriksson, Uppsala (SE); Per Dahlberg, Uppsala (SE); Simon Kinloch, Hemel Hempstead (GB); Magnus Wallen, Uppsala (SE); Jonas Ove Norling, Uppsala (SE); Martin Orbe, Uppsala (SE)

(73) Assignee: General Electric Company, Schenectady, NY (US)

(*) Notice: Subject to any disclaimer, the term of this patent is extended or adjusted under 35 U.S.C. 154(b) by 568 days.

(21) Appl. No.: 14/037,802

(22) Filed: Sep. 26, 2013

(65) Prior Publication Data
US 2015/0086476 A1 Mar. 26, 2015

(51) Int. Cl.
| | | |
|---|---|---|
| *B25J 21/02* | (2006.01) | |
| *A61K 51/00* | (2006.01) | |
| *B01J 19/00* | (2006.01) | |
| *C07B 59/00* | (2006.01) | |

(52) U.S. Cl.
CPC .............. *A61K 51/00* (2013.01); *B01J 19/00* (2013.01); *C07B 59/00* (2013.01)

(58) Field of Classification Search
CPC .... B01L 1/00; B01L 1/02; B01L 1/025; B01L 1/04; B01L 1/50; B25J 21/00; B25J 21/02
USPC .............................. 422/567; 454/49, 56, 187
See application file for complete search history.

(56) References Cited

U.S. PATENT DOCUMENTS

| | | | |
|---|---|---|---|
| 5,219,215 A | * | 6/1993 | Akagawa .................. B01L 9/02 312/1 |
| 7,586,102 B2 | | 9/2009 | Mourtada et al. |
| 7,717,774 B2 | * | 5/2010 | Rothbauer et al. ........... 454/187 |
| 7,829,032 B2 | | 11/2010 | Van Dam et al. |
| 8,071,035 B2 | | 12/2011 | Elizarov et al. |
| 8,173,073 B2 | | 5/2012 | Elizarov et al. |
| 8,233,580 B2 | | 7/2012 | Sedeschi |
| 8,273,300 B2 | | 9/2012 | Elizarov et al. |

(Continued)

FOREIGN PATENT DOCUMENTS

| | | |
|---|---|---|
| EP | 1736997 | 8/2011 |
| EP | 2511006 A2 | 10/2012 |

(Continued)

OTHER PUBLICATIONS

International Search Report and Written Opinion for corresponding PCT application No. PCT/US2014/050054 dated Nov. 3, 2014; 8 pages.

*Primary Examiner* — Jill Warden
*Assistant Examiner* — Dwayne K Handy
(74) *Attorney, Agent, or Firm* — Dean D. Small; The Small Patent Law Group, LLC.

(57) ABSTRACT

A standalone radiopharmaceutical preparation hotcell for preparing a radiopharmaceutical includes a housing and a plurality of compartments defined within the housing. The plurality of compartments including at least a pharmaceutical synthesizing and dispensing compartment and a different second compartment, the synthesizing and dispensing compartment being maintained at a first pressure and the second compartment being maintained at a different second pressure using a compartment pressurization system.

20 Claims, 4 Drawing Sheets

(56) References Cited

U.S. PATENT DOCUMENTS

| | | |
|---|---|---|
| 8,435,454 B2 | 8/2013 | Elizarov et al. |
| 2004/0086437 A1* | 5/2004 | Jackson .................. 422/903 |
| 2006/0039522 A1 | 2/2006 | Bars et al. |
| 2008/0035542 A1 | 2/2008 | Mourtada et al. |
| 2008/0233018 A1 | 9/2008 | van Dam et al. |
| 2008/0233653 A1 | 9/2008 | Hess et al. |
| 2008/0242915 A1 | 10/2008 | Jackson et al. |
| 2009/0036663 A1 | 2/2009 | Elizarov et al. |
| 2010/0087009 A1 | 4/2010 | Li et al. |
| 2010/0121184 A1 | 5/2010 | Dhawale et al. |
| 2010/0286512 A1 | 11/2010 | Dhawale et al. |
| 2011/0097245 A1 | 4/2011 | Elizarov et al. |
| 2012/0077429 A1* | 3/2012 | Wernimont et al. .......... 454/187 |
| 2012/0107175 A1* | 5/2012 | Satyamurthy .......... B01J 19/004 422/68.1 |
| 2012/0223246 A1 | 9/2012 | Stephani et al. |
| 2012/0321026 A1 | 12/2012 | Norling et al. |

FOREIGN PATENT DOCUMENTS

| | | |
|---|---|---|
| WO | 2005057589 | 6/2005 |
| WO | 2008021302 | 2/2008 |
| WO | 2008091694 | 7/2008 |
| WO | 2008091694 A2 | 7/2008 |
| WO | 2008128201 | 10/2008 |
| WO | 2012031299 | 3/2012 |

\* cited by examiner

SYSTEMS, METHODS AND APPARATUS FOR MANUFACTURING RADIOISOTOPES

BACKGROUND OF THE INVENTION

The subject matter disclosed herein relates generally to radioisotopes used in medical imaging, and more particularly to systems, methods, and an apparatus for preparing the radioisotope to be used in a medical imaging procedure.

In conventional imaging procedures, an individual dose of a premeasured radioisotope or radioisotope is administered to an individual patient. The individual premeasured radioisotope is prepared by a radioisotope supplier (commonly called a radiopharmacy). A cyclotron is used most commonly to prepare the radioisotope. The radioisotope is delivered to a medical facility that administers the individual premeasured radioisotope as a radiopharmaceutical. The individual premeasured radioisotope is prepared by the radioisotope supplier in accordance with a prescription from a physician. The prescription includes a prescribed amount of radioactivity at a future time and a date of the prescribed administration in a known volume of a liquid suitable for injection into a living subject.

The conventional process of radioisotope production in a cyclotron performed by a radioisotope supplier is as follows: The radioisotope supplier irradiates a target material, such as water, in the cyclotron with a beam of protons or deuterons to produce a desired amount of radioactivity in the target material, referred to herein as radioactive water. Typically, the cyclotron is located in a dedicated room. Examples of cyclotron produced radioisotopes include nitrogen-13, fluorine-18, carbon-11 and oxygen-15.

Often, compounds are bond to the radioactive water to produce radioisotopes such as fluorodeoxyglucose (FDG) which is produced using fluorine-18. Other radioisotopes include nitrogen-13 ammonia which is used in myocardial applications, carbon-11 tracers which are commonly used in neurologic applications; and oxygen-15 gas as well as tracers derived from it which are commonly used in blood flow applications. More specifically, the radioactive water is typically delivered to a separate room that includes a synthesizing device for bonding the compound to the radioactive water and a dispensing station for dividing the radioisotope into individual doses that are stored in individual vials or containers.

In general, the room containing the synthesizing device and the dispensing station is designated as a clean room. More specifically, the clean room is maintained to ensure compliance with, for example, International Organization for Standardization 7 (ISO 7) and Good Manufacturing Practice (GMP) guidelines. However, because of the size of the typical clean room, it is often time consuming and expensive to maintain the clean room in accordance with ISO 7 and GMP guidelines. More specifically, it is often time consuming for personnel to maintain the filtering system and cleanliness of the various equipment installed in the clean room in accordance with the ISO 7 as published by the International Organization for Standardization and is incorporated by reference herein and GMP guidelines as published by the Federal Drug Administration (FDA) and are also incorporated herein by reference.

BRIEF DESCRIPTION OF THE INVENTION

In one embodiment, a standalone radiopharmaceutical preparation apparatus for preparing a radiopharmaceutical is provided. The apparatus includes a housing and a plurality of compartments defined within the housing. The plurality of compartments including at least a pharmaceutical synthesizing and dispensing compartment and a different second compartment, the synthesizing and dispensing compartment being maintained at a first pressure and the second compartment being maintained at a different second pressure using a compartment pressurization system.

In another embodiment, a radio pharmaceutical manufacturing system is provided. The system includes an integrated hotcell including a first compartment and a second compartment and a compartment pressurization system pressurizing the first and second compartments. The system further includes a controller coupled to the integrated hotcell and the compartment pressurization system, the controller configured to receive a predetermined operational pressure for each of the first and second compartments and operate the compartment pressurization system to maintain an operational pressure within the of the first and second compartments at the predetermined operational pressures.

In a further embodiment, a method of preparing a radiopharmaceutical using a standalone radiopharmaceutical preparation apparatus is provided. The method includes receiving a batch of radioactive water into a first pressurized compartment within the apparatus, utilizing a synthesizer within the first pressurized compartment to prepare a batch of radiopharmaceutical, and subdividing the batch of radiopharmaceutical into individual doses using a dispensing unit installed within the first pressurized compartment.

DETAILED DESCRIPTION OF THE INVENTION

Figure 1:
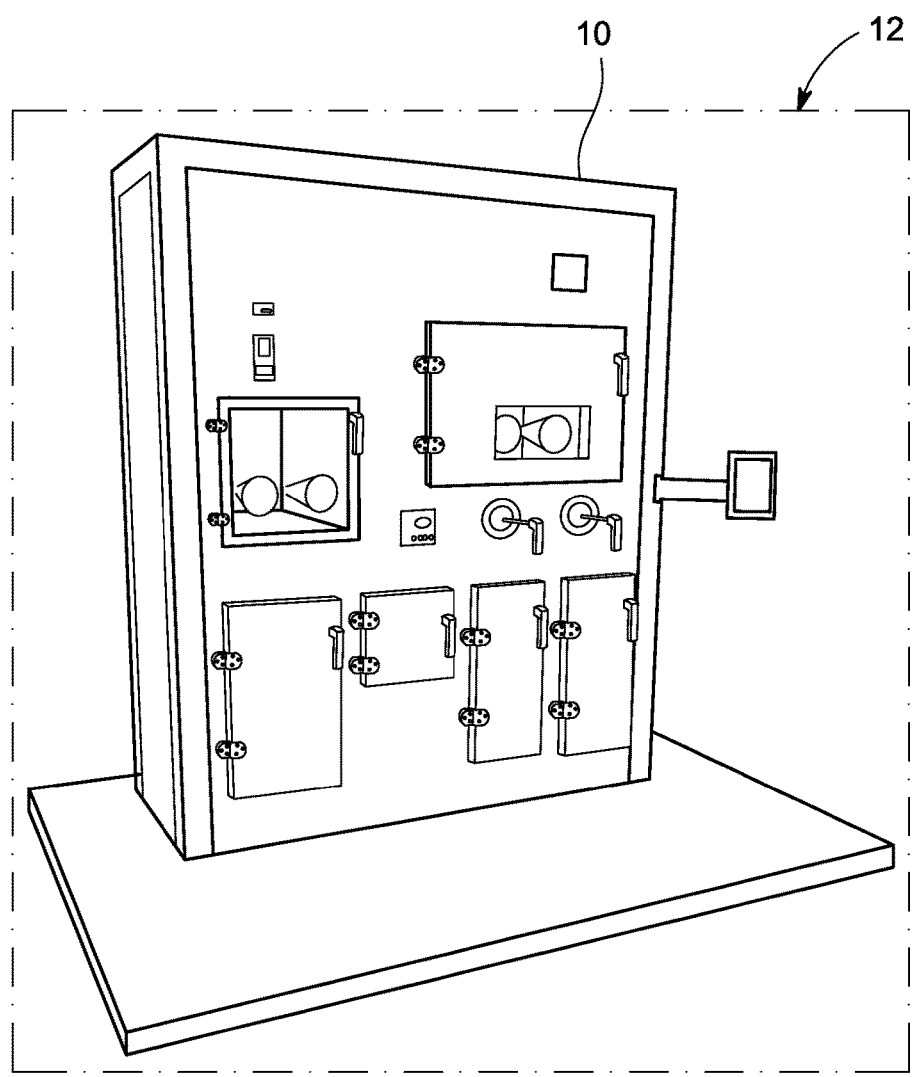
FIG. 1 is a pictorial view of an exemplary integrated hotcell formed in accordance with various embodiments.

The following detailed description of certain embodiments will be better understood when read in conjunction with the appended drawings. To the extent that the figures illustrate diagrams of the functional modules of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide an apparatus and methods for providing a standalone radiopharmaceutical preparation apparatus, also referred to herein as an integrated hotcell, to facilitate manufacturing and dispensing a radiopharmaceutical that may be injected into a patient, for example during a medical imaging procedure. As used herein an integrated hotcell means a standalone device that includes a plurality of individual compartments that are isolated from other compartments within the integrated hotcell, using doors or hatches, to reduce and/or eliminate the transfer of particulate matter or contaminants from being transferred to adjacent compartments within the integrated hotcell. In operation, the integrated hotcell therefore functions as a clean room like environment having a reduced size that may be located in any desired room within a facility. Thus, the integrated hotcell eliminates the need to designate an entire room in the facility as a clean room while maintaining radiation safety regulatory requirements required for the production of radiopharmaceuticals, e.g. such as radio labeled pharmaceuticals fabricated under Good Manufacturing Practice (GMP) guidelines.

In various embodiments, the integrated hotcell is fabricated to include a plurality of individual compartments, wherein each compartment is radioactively isolated from, and maintained at a select partial pressure relative to, other compartments in the integrated hotcell. In various embodiments, at least one of the compartments is positively pressurized, e.g. maintained at a positive partial pressure, to prevent ingress of contaminants from other compartments within the integrated hotcell and also prevent ingress of contaminants from the external environment surrounding the integrated hotcell. Moreover, at least one of the compartments is maintained at a negative partial pressure, e.g. a partial vacuum. In some embodiments, each of the compartments adjacent to and/or surrounding the positively pressurized compartment are maintained at a negative pressure such that the pressurized compartment functions as a clean room like environment in accordance with ISO 7 and the GMP guidelines.

FIG. 1 is a pictorial view of an exemplary integrated hotcell 10 formed in accordance with various embodiments. The term hotcell generally refers to a shielded nuclear containment chamber that is used in, for example, the medical industry. In various embodiments described herein, the term integrated hotcell means a standalone apparatus that includes a plurality of individual compartments, wherein at least one of the compartments is designated as a hotcell and thus includes a radiation shield to enable a radiopharmaceutical to be manufactured therein. The compartment designated as the hotcell is also referred to herein as the synthesis/dispensing compartment and is maintained as a clean room like environment. In the exemplary embodiment, the integrated hotcell 10 is fabricated as a stand-alone unit that may be installed within a room 12. The room 12 may be, for example, a room that is located in a medical imaging facility, hospital, and/or facility housing a cyclotron. It should therefore be realized that the integrated hotcell 10 has a volume that is smaller than a volume of the room 12 housing the integrated hotcell 10. In various embodiments, the integrated hotcell 10 includes a plurality of compartments 14 wherein at least one of the compartments 14 is designated as the hotcell and includes equipment to manufacture the radiopharmaceutical. Additionally, because the compartment designated as the hotcell is used to manufacture the pharmaceutical, the compartment is also maintained as a clean room like environment in accordance with the ISO 7 and the GMP guidelines. The configuration of the compartments 14 and the function of the compartments 14 are described in more detail below.

Figure 2:
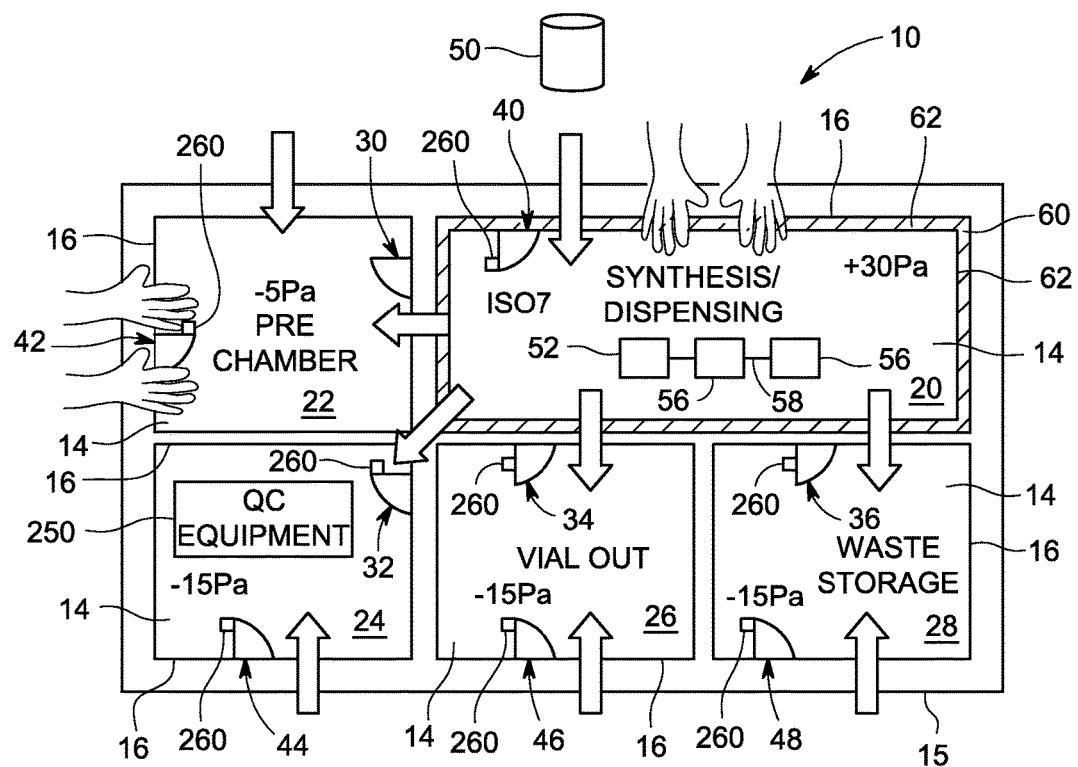
FIG. 2 is a schematic illustration of the integrated hotcell shown in FIG. 1 in accordance with various embodiments.

FIG. 2 is a schematic illustration of the integrated hotcell 10 shown in FIG. 1 in accordance with various embodiments. As described above, the integrated hotcell 10 includes a housing 15 and a plurality of walls 16 that are installed within the housing 15 to form a plurality of compartments 14 within the hotcell 10. In the exemplary embodiment, each compartment 14 is therefore defined by six walls 16 that define the upper surface, lower surface, and sides of each compartment 14. The plurality of compartments 14 may include, for example, a synthesis/dispensing compartment 20, a prechamber compartment 22, a quality control compartment 24, a vial out compartment 26, and a waste storage compartment 28. It should be realized that the integrated hotcell 10 may include additional compartments that are not shown and that the compartments 22, 24, 26, and 28 are examples of compartments that me be included within the integrated hotcell 10. The operation of the compartments 20, 22, 24, 26, and 28 are described in more detail below.

The integrated hotcell 10 also includes a plurality of intercompartment doors or hatches that provide intercompartment access between the synthesis/dispensing compartment 20 and the prechamber compartment 22, the quality control compartment 24, the vial out compartment 26, and the waste storage compartment 28. For example, the integrated hotcell 10 includes an intercompartment door 30 that is installed between the synthesis/dispensing compartment 20 and the prechamber compartment 22 to enable materials to be transferred between the synthesis/dispensing compartment 20 and the prechamber compartment 22. The integrated hotcell 10 also includes an intercompartment door 32 between the synthesis/dispensing compartment 20 and the quality control equipment compartment, an intercompartment door 34 between the synthesis/dispensing compartment 20 and the vial out compartment 26, and an intercompartment door 36 between the synthesis/dispensing compartment 20 and the waste storage compartment 28. In operation, the intercompartment doors 30, 32, 34, and 36 each include seals, not shown, that facilitate maintaining the synthesis/dispensing compartment 20 within the ISO 7 and GMP guidelines. For example, when one of the intercompartment doors 30, 32, 34, 36, or 38 is in the open position, the positive partial pressure in the synthesis/dispensing compartment 20 facilitates preventing contaminants within the compartment surround the synthesis/dispensing compartment 20 from entering the synthesis/dispensing compartment 20. Moreover, when the intercompartment doors 30, 32, 34, 36, or 38 are in the closed position, the seal attached to each intercompartment door substantially prevents contaminants from leaking into the synthesis/dispensing compartment 20.

The integrated hotcell 10 may also include a plurality of external doors to enable various materials to be positioned within or removed from the various compartments 14. For example, the integrated hotcell 10 may include an external door 40 to enable a batch of radioactive water 50 to be positioned within the synthesis/dispensing compartment 20. The integrated hotcell 10 may also include an external door 42 to enable materials to be positioned in or removed from the prechamber compartment 22, an external door 44 to enable materials to be positioned in or removed from the quality control equipment compartment 24, an external door 46 to enable materials to be positioned in or removed from the vial out compartment 26, and an external door 48 to enable materials to be positioned in or removed from the waste storage compartment 28. In operation, the intercompartment doors 30, 32, 34, 36, or 38 provide intercompartment access to various compartments from within the integrated hotcell 10. Moreover, the external doors 40, 42, 44, 46, and 48 enable access to the various compartments from outside the integrated hotcell 10.

In operation, the synthesis/dispensing compartment 20 is utilized to receive a batch of radioactive water 50. Synthesizing unit 52 within the synthesis/dispensing compartment 20 is then utilized to bond the radioactive water 50 with a sugar molecule, for example, to fabricate a radiopharmaceutical that may be injected into a patient prior to a medical imaging procedure for example.

The synthesis/dispensing compartment 20 also includes a dispensing unit 54 that is utilized to dispense the radiopharmaceutical. More specifically, the radioactive water 50 may be of sufficient quantity to manufacture multiple doses of the radiopharmaceutical. Thus, in operation, the dispensing unit 54 is configured to enable an operator to produce and package multiple doses of the radiopharmaceutical. Thereafter, the vials containing individual doses of radiopharmaceutical may each be packaged in an individual lead-shielded container. The synthesis equipment 52 and the dispensing unit 54 are described in more detail below.

It should therefore be realized that the synthesis/dispensing compartment 20 is utilized to both receive the radioactive water 50 and to manufacture a plurality of doses of the radiopharmaceutical using the radioactive water 50 received from the cyclotron. Moreover, it should be realized that the synthesis/dispensing compartment 20 is configured and operated in accordance with ISO 7 and GMP guidelines.

Accordingly, in the exemplary embodiment, the synthesis/dispensing compartment 20 is formed as a radiation shielded compartment to facilitate reducing/and or eliminating radioactive materials, that exceed the guidelines set forth in ISO 7 and the GMP guidelines, from being released into any of the compartments surrounding the synthesis/dispensing compartment 20, e.g. the compartments 22, 24, 26, and 28 or into the atmosphere within the room 12. In one embodiment, the radiation shielding may be embodied as a lead radiation shield 60 that is configured to encapsulate the synthesis/dispensing compartment 20. More specifically, the synthesis/dispensing compartment 20 includes four sidewalls 62, a top surface, and a bottom surface, not shown. Accordingly, the lead radiation shield 60 is formed on the four sidewalls 62, the top surface, and the bottom surface forming the synthesis/dispensing compartment 20 such that each of the inner surfaces of the synthesis/dispensing compartment 20 are covered by the lead radiation shield 60. In various embodiments, other compartments 14 may also include a lead shield. For example, the waste storage compartment 28, among others, may include a lead shield (not shown).

To further ensure that the synthesis/dispensing compartment 20 is maintained an operated in accordance with the ISO 7 and GMP guidelines, the integrated hotcell further includes a ventilation system operable to maintain at least some of the compartments 14 at different operational pressures.

Figure 3:
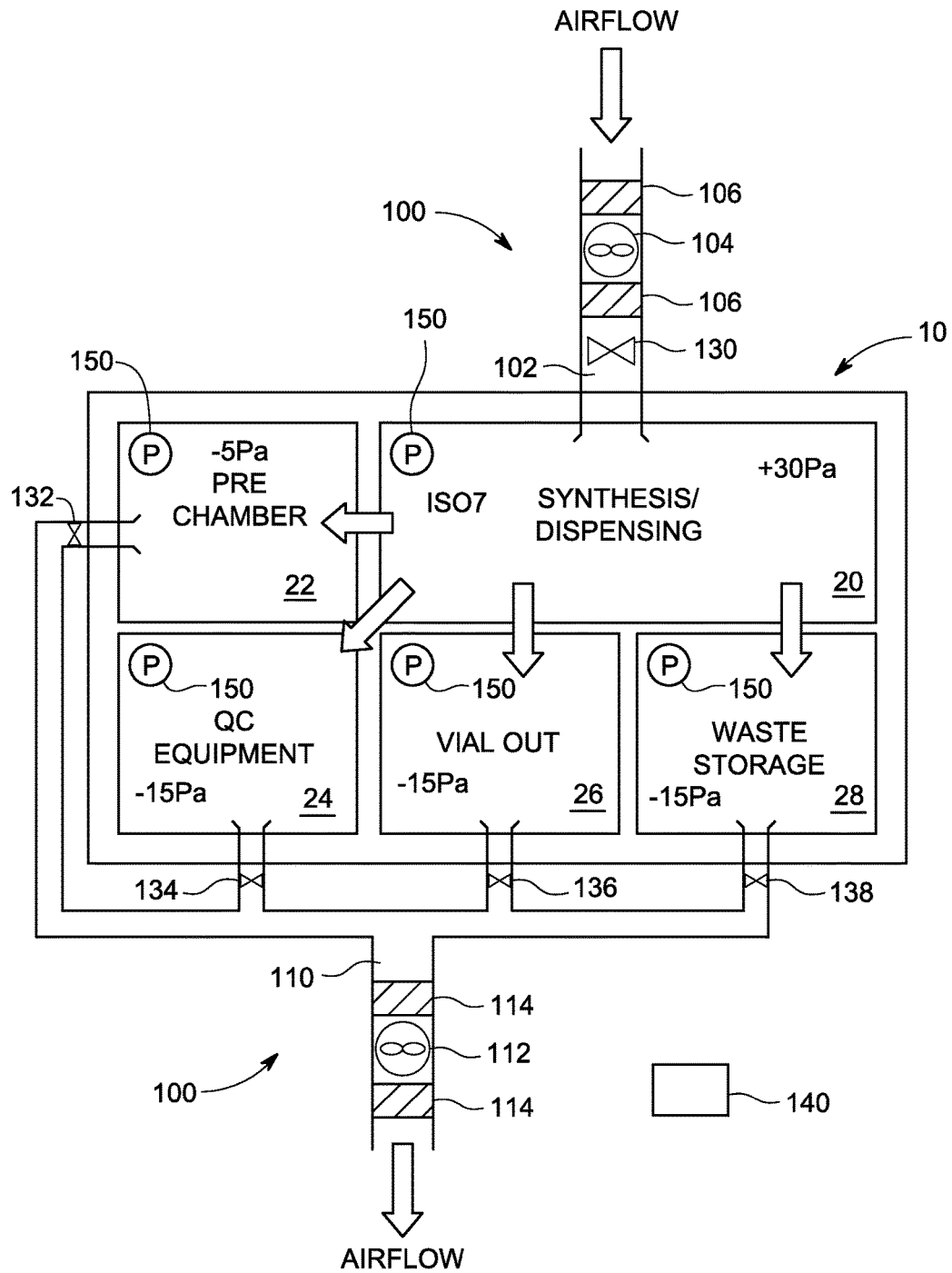
FIG. 3 is schematic illustration of a compartment pressurization system formed in accordance with various embodiments.

For example, FIG. 3 is a schematic illustration of an exemplary compartment pressurization system 100 that may be utilized with and/or form part of the integrated hotcell 10. In operation, the compartment pressurization system 100 is utilized to maintain the compartments 14 at predetermined air pressures. In various embodiments, the compartment pressurization system 100 is configured to maintain at least one of the compartments at a positive pressure compared to atmospheric pressure and also maintain at least one of the compartments at a negative pressure or vacuum compared to atmospheric pressure. For example, in some embodiments, the compartment pressurization system 100 is configured to maintain the synthesis/dispensing compartment 20 at positive air pressure P1 to facilitate inhibiting contaminants from the atmosphere from being introduced into the synthesis/dispensing compartment 20 when, for example, the door 40 is opened such that the synthesis/dispensing compartment 20 is maintained as a clean room like environment, e.g. maintained within the ISO 7 and GMP guidelines. In various embodiments, the partial pressure P1 is within a range of approximately 20 Pa to approximately 40 Pa. In the exemplary embodiment, the partial pressure P1 is approximately 30 Pa. More specifically, the compartment pressurization system 100 is configured to maintain the synthesis/dispensing compartment 20 at a greater differential pressure P1, than the partial pressure P2 being maintained in the compartments 22, 24, 26, and 28. In various embodiments, the partial pressure P2 is within a range of approximately −5 Pa to approximately −25 Pa. In the exemplary embodiment, the partial pressure P2 is approximately −15 Pa. In various embodiments, the compartments 22, 24, 26, and 28 may be maintained at the same or common pressure P2. Optionally, at least one of the compartments 22, 24, 26, and 28 may be maintained at a different partial pressure P3. For example, in one embodiment the compartments 24, 26, and 28 may be maintained at the partial pressure P2 and the chamber 22 may be maintained at a partial pressure P3. In various embodiments, the partial pressure P3 is within a range of approximately 0.0 Pa to approximately −10 Pa. In the exemplary embodiment, the partial pressure P3 is approximately −5 Pa. As used herein, a clean room like environment is defined as an environment that has a relatively low level of contaminants, such as dust, radiation particles, microbes, etc. Thus, compartment pressurization system 100 is utilized to maintain a clean room like environment in the synthesis/dispensing compartment 20 by controlling a level of contamination within the synthesis/dispensing compartment 20 in accordance with the guidelines as set forth in ISO 7 and the GMP guidelines. The compartment pressurization system 100 is also configured to maintain at least one of the compartments 14 at a negative pressure compared to atmospheric pressure, e.g. vacuum, such that when a door between the synthesis/dispensing compartment 20 and one of the other compartments is opened, any potential contaminants within the other compartments are not introduced into the synthesis/dispensing compartment 20. For example, the prechamber 22 may be maintained at a negative pressure, such that when the door 30 between the prechamber 22 and the synthesis/dispensing compartment 20 is opened, any contaminants within the prechamber are not introduced into the synthesis/dispensing compartment 20.

In the illustrated embodiment, the compartment pressurization system 100 includes a positively pressurized ducting system 102 and a fan 104. In operation, the fan 104 is configured to channel air into the synthesis/dispensing compartment 20 to maintain the synthesis/dispensing compartment 20 at a positive pressure as described above. More specifically, a controller 140, described in more detail below, is configured to adjust an operational speed of the fan 104 to maintain the synthesis/dispensing compartment 20 at the positive pressure P1. For example, an operational speed of the fan 140 may be increased to increase the partial pressure P1 within the synthesis/dispensing compartment 20. Optionally, the operational speed of the fan 140 may be reduced to reduce the partial pressure P1 within the synthesis/dispensing compartment 20. In various embodiments, the positively pressurized ducting system 102 may also include filters 106 or other devices to filter the air being channeled into the synthesis/dispensing compartment 20. The filters 106 may be embodied as, for example, high-efficiency particulate air (HEPA) filters, ultra low penetration (ULPA) filters, and/or charcoal filters.

The compartment pressurization system 100 also includes a negatively pressurized ducting system 110 and a fan 112. In operation, the fan 112 is configured to channel air from at least one of the compartments 22, 24, 26, and 28 to maintain a negative pressure or vacuum as described above. In various embodiments, the negatively pressurized ducting system 110 may also include filters 114 or other devices to filter the air being removed from the compartments 22, 24, 26, and/or 28. The filters 114 may embodied as, for example, high-efficiency particulate air (HEPA) filters and/or ultra low penetration (ULPA) filters. It should be realized that the configuration of the ducting systems 102 and 110 shown in FIG. 3 are exemplary only, and that the positive and negative pressures may be maintained within the compartments 20, 22, 24, 26, and 28 using a variety of different ducting systems and fan configurations, and FIG. 3 illustrates one such configuration.

The compartment pressurization system 100 further includes a plurality of valves for controlling the movement or flow of air through both the positively pressurized ducting system 102 and he negatively pressurized ducting system 110. For example, the compartment pressurization system 100 includes a valve 130 for controlling a volume of airflow being channeled into the synthesis/dispensing compartment 20. The compartment pressurization system 100 includes a valve 132 for controlling a volume of airflow being discharged from compartment 22, a valve 134 for controlling a volume of airflow being discharged from compartment 24, a valve 136 for controlling a volume of airflow being discharged from compartment 26, a valve 138 for controlling a volume of airflow being discharged from compartment 28.

In the exemplary embodiment, the valves 130, 132, 134, 136, and 138 are implemented as electrically actuated valves that may be controlled by a controller 140. The valves the valves 130, 132, 134, 136, and 138 are operable in either a fully open configuration, a fully closed position, or any operational position between fully open and fully closed. Accordingly, the valve 130 may be operated to enable airflow to be supplied to the compartment 20 to maintain a positive pressure on the compartment 20. Moreover, the valves 132, 134, 136, and 138 may be operated to enable airflow to be discharged from the compartments 22, 24, 26, and 28, to maintain a negative pressure on the compartments 22, 24, 26, and 28 respectively. Thus, the valves 130, 132, 134, 136, and 138 operate to regulate a quantity of being input to or discharged from the compartments 20, 22, 24, 26, and 28 to either maintain a positive or negative pressure within the compartments 20, 22, 24, 26, and 28.

It should be realized that although the compartment pressurization system 100 illustrated in FIG. 3 represents one exemplary embodiment, wherein the ducting systems 102 and 110, and the various other components forming the compartment pressurization system 100 and the controller 140 are located externally from the integrated hotcell 10 to form a pharmaceutical manufacturing system, Moreover, some or all of the components forming the compartment pressurization system 100 and the controller 140 may be installed internally within the integrated hotcell 10.

The compartment pressurization system 100 further includes a plurality of sensors that are configured to provide information to the controller 140 to enable the controller 140 to regulate the pressure within the compartments 20, 22, 24, 26, and 28. In various embodiments, the sensors may include for example, a plurality of compartment pressure sensors 150, wherein at least one compartment pressure sensor 150 is installed in each of the respective compartments 20, 22, 24, 26, and 28. In operation, the compartment pressure sensors 150 sense the pressure within each of the compartments 20, 22, 24, 26, and 28 and provide real-time feedback to the controller 140 to enable the controller 140 to adjust or modify the operational pressure individually within each of the respective compartments 20, 22, 24, 26, and 28.

In operation, the outputs from the pressure sensors 150 are input to the controller 140. In one embodiment, the controller 140 utilizes the inputs from the pressure sensors 150 to facilitate maintaining, in real time, the partial pressures P1, P2, and/or P3 within the compartments 20, 22, 24, 26, and 28 within a predetermined pressure entered by the operator into the controller 140 or at a predetermined pressure level which may also be entered by the operator into the controller 140.

In various embodiments, the controller 140 is mounted proximate to the integrated hotcell 10 to enable an operator to provide inputs to the controller 140. The controller 140 may be embodied as a computer. As used herein, the term "computer" may include any processor-based or microprocessor-based system including systems using microcontrollers, reduced instruction set computers (RISC), application specific integrated circuits (ASICs), field programmable gate array (FPGAs), logic circuits, and any other circuit or processor capable of executing the functions described herein. The above examples are exemplary only, and are thus not intended to limit in any way the definition and/or meaning of the term "computer".

More specifically, the controller 140 may receive an input by the operator to maintain the pressure within the synthesis dispensing compartment 20 at a first predetermined pressure, which in the exemplary embodiment is negative. For example, in one embodiment, the operator may instruct the controller 140 to maintain the synthesis/dispensing compartment 20 at a predetermined pressure of 30 Pascals (Pa). In response, the controller 140 operates the fan 104 and/or the valve 130 to maintain the pressure within the synthesis/dispensing compartment 20 at approximately 30 Pa.

Moreover, the controller 140 may receive an input by the operator to maintain the pressure within one of the compartments 22, 24, 26, and/or 28 at a second different predetermined pressure, which in the exemplary embodiment is positive. For example, in one embodiment, the operator may instruct the controller 140 to maintain the prechamber compartment at −5 Pa, maintain the quality control equipment compartment at −15 Pa, maintain the vial out compartment at −15 Pa, and also maintain the waste storage compartment 28 at −15 Pa. In response, the controller 140 operates the fan 112 and/or the valves 132, 134, 136 and/or 138 to maintain the pressure within the respective compartments 22, 24, 26, and 28 at the predetermined pressures. It should be realized that the predetermined pressures described herein are exemplary only, and that the controller 140 may be utilized to maintain the pressures within the compartments 20, 22, 24, 26, and 28 at any desired pressure.

It should be noted that the various embodiments or portions thereof, such as the controller 140 may be implemented in hardware, software or a combination thereof. The various embodiments and/or components, for example, the controller 140 may be implemented as part of one or more computers or processors. The controller 140 may include a plurality of ports to enable displays, input devices, or other user interfaces to connect to the controller 140. The controller 140 may include Random Access Memory (RAM) and Read Only Memory (ROM). The controller 140 may further include a storage device, which may be a hard disk drive or a removable storage drive such as a solid state drive, optical disk drive, and the like. The storage device may also be other similar means for loading computer programs or other instructions into the controller 140. In various other embodiments, the controller 140 may be configured to receive inputs via the Internet using for example, a Wi-Fi connection or a hard-wired connection. Additionally, the controller 140 may be configured to couple to a local area network (LAN) and receive inputs from various devices either installed on the aircraft or located remotely form the aircraft. In further embodiments, the controller 140 may receive inputs from a cellular phone device or any other portable touchscreen device, such as a portable laptop computer, etc.

The controller 140 executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

Figure 4:
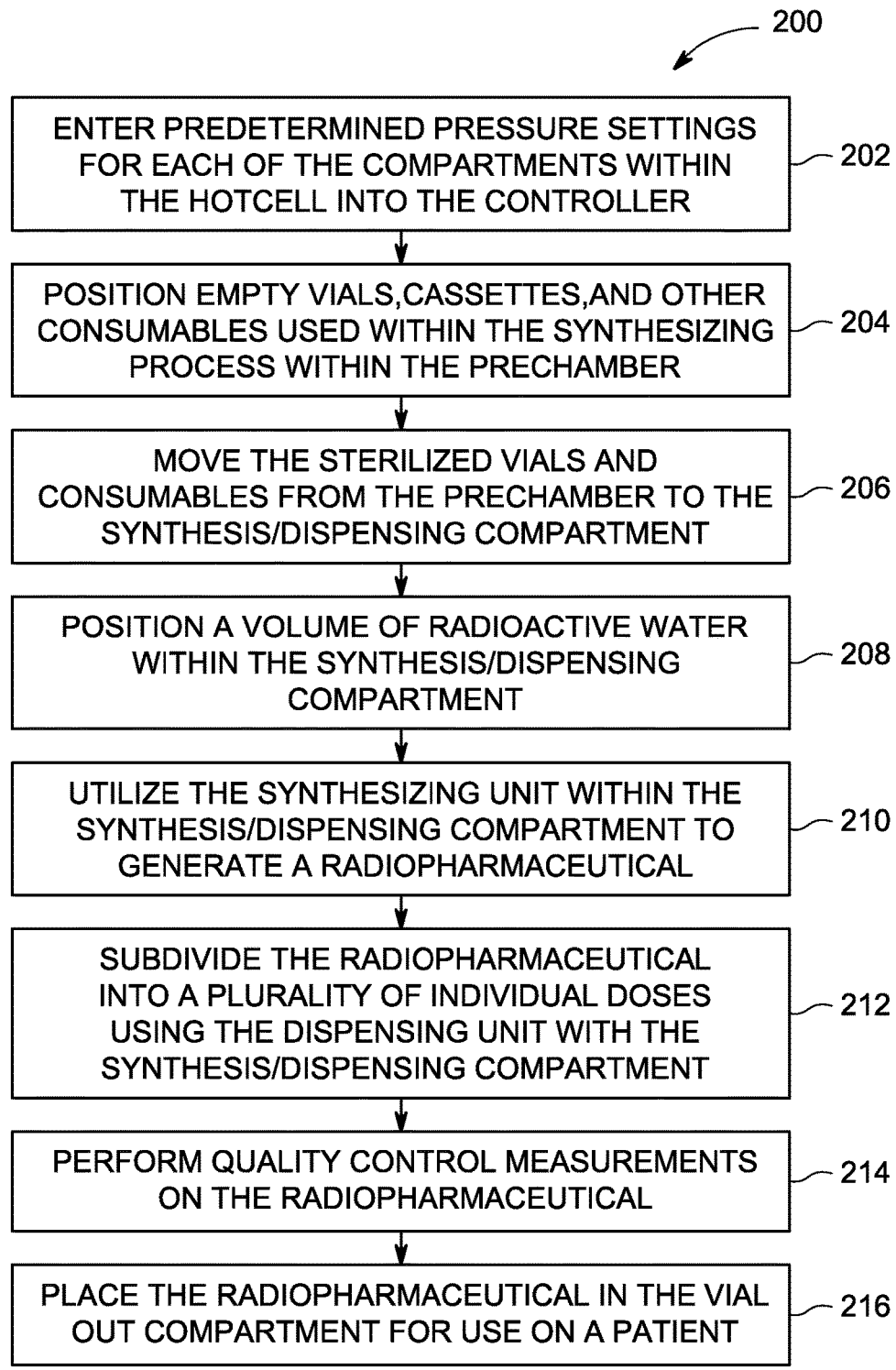
FIG. 4 a flowchart of a method of manufacturing a radiopharmaceutical in accordance with various embodiments.

FIG. 4 is a flowchart illustrating an exemplary method 200 of manufacturing a radiopharmaceutical using the integrated hotcell 10 described above.

At 202, predetermined pressure settings for each of the compartments 20, 22, 24, 26, and 28 within the hotcell 10 are entered into the controller 140. In response, the controller 140 operates the compartment pressurization system 100 to maintain each compartment within the predetermined pressure range or at the predetermined pressure level. For example, assume that the operator enters information into the controller 140 that instructs the controller 140 to maintain the partial pressure P1 within the synthesis/dispensing compartment 20 at +30 Pa. In the exemplary embodiment, the controller 140 may position the valve 130 to an open position. Additionally, the controller 140 may activate the fan 104 to channel air into the synthesis/dispensing compartment 20 until the partial pressure within the synthesis/dispensing compartment 20 is approximately +30 Pa based on an input received from the pressure sensor 150 installed within the synthesis/dispensing compartment 20. Once, the controller 140 determines that the partial pressure P1 within the synthesis/dispensing compartment 20 is substantially equal to the predetermined level entered by the user, the controller 140 may reduce the operational speed of the fan 104 to facilitate maintaining the partial pressure P1 at the predetermined pressure. Optionally, the controller may deactivate the fan 130. In various embodiments, the controller 140 is configured to activate or deactivate the fan 104 to maintain the partial pressure P1 at the predetermined level entered by the operator.

At 204, empty vials, cassettes, and other consumables used within the synthesizing process are positioned within the prechamber 22 using the external door 42. More specifically, the external door 42 is opened causing the partial pressure P3 within the prechamber to return to atmospheric pressure. In various embodiments, the external door 42 and other intercompartment and external doors described herein may have a door position sensor, such as position sensor 260 shown in FIG. 2, that provides a signal to the controller 140 indicating that the door is in the open or closed position. For example, when the door sensor 260 senses that the external door 22 is opened, the controller 140 may deactivate the fan 112. The empty vials, cassettes, and other consumables are then positioned within the prechamber 22 and the external door 42 is closed. The controller 140 senses that the external door 42 is now in the closed position and reactivates the fan 112. The fan 112 is then operated to maintain the partial pressure P3 within the prechamber 22 at the predetermined level entered by the operator. It should be realized that the various doors described herein may each include a door position sensor that output a signal to the controller 140 indicating a position of the door. The controller 140 may utilize the inputs from the door position sensors to activate and/or deactivate the fans 102 or 112, and/or to open and or close the valves. In operation, the prechamber includes sterilization equipment or devices that function to sterilize the vials and other consumables.

At 206, the sterilized vials and consumables are moved from the prechamber 22 to the synthesis/dispensing compartment 22. More specifically, the intercompartment door 30 is opened, the vials and consumables are then moved through the intercompartment door 30 into the synthesis/dispensing compartment 22 and the intercompartment door 30 is then closed.

At 208, a batch of radioactive water, such as the batch of radioactive water 50, is positioned within the integrated hotcell 10. More specifically, the batch of radioactive water 50 is positioned within the synthesis/dispensing compartment 20. As described above, the batch of radioactive water 50 is generated using a cyclotron that may be located in the same building as the integrated hotcell 10 or in a different building.

At 210, the synthesizing unit 52 is utilized to chemically modify the radioactive water 50 to generate a radiopharmaceutical that may be injected into a patient prior to a medical imaging procedure, for example. For example, in one embodiment, the synthesizer 52 is configured to chemically bond the radioactive water 50 to a biological compound to generate a radiopharmaceutical 56 as shown in FIG. 2. In various embodiments, the radiopharmaceutical may be embodied as, for example, a FDG.

At 212, the radiopharmaceutical 56 is then subdivided into individual doses using the dispensing unit 54 shown in FIG. 2. In embodiments where the radiopharmaceutical 56 has a short half life (e.g. carbon-1, oxygen-15 and nitrogen-13), the transfer may be performed through a line that shields radioactivity, such as a lead-shielded line 58 as shown in FIG. 2. In embodiments where the radiopharmaceutical 56 has a longer half life (e.g. flourine-18) the transfer may be performed by placing the multidose portion of the radiopharmaceutical 56 in a reservoir (not shown) and transporting the reservoir to the dispensing station 54 and emptying the contents of the reservoir into the dispensing station 54. Regardless of how the material is transported, the multidose portion of radiopharmaceutical 56 is stored in the dispensing station 54. Optionally, the radiopharmaceutical 56 may be dispensed into vials manually by the operator.

In the illustrated embodiment, the integrated hotcell 10 also includes the quality control compartment 24 as described above. Accordingly, and in various embodiments, at 214, quality control (QC) equipment 250 installed within the quality control compartment 24 may be utilized to monitor the amount of radioactivity and perform other measures of quality and quantity of the multidose portion of radiopharmaceutical 56 that is stored in the dispensing unit 54. For example, the QC equipment 250 may be utilized the measure the radionucleic and chemical purity of the radiopharmaceutical 56. In some embodiments, quality control monitoring, analysis and verification may be performed at particular time intervals or for particular production batches or for one representative sample of bulk produced radiopharmaceutical 56. The time intervals and batches may be predetermined and modified by an operator. In some embodiments, the QC equipment 250 indicates that quality of the radiopharmaceutical 56 is below acceptable minimum standards, the controller 140 may provide a visual or audible indication to the operator. Moreover, the QC equipment 250 may instruct the dispensing unit 54 to purge the radiopharmaceutical 56. More specifically, the QC equipment 250 may instruct the dispensing unit 54 to transfer the unacceptable radiopharmaceutical 56 to the waste storage compartment 28 for disposal at a later time.

At 216, the radiopharmaceutical 54 is placed in the vial out compartment 26. The vial may then be retrieved by a technician and injected into a patient prior to performing a medical imaging procedure. Such medical imaging procedures may include for example, imaging a patient with a Positron Emission Tomography (PET) imaging system or a Single Photon Emission Computed Tomography (SPECT) imaging system, for example.

In various embodiments, the controller 140 may be utilized to operate the synthesizing unit 52 and the dispensing unit 54. More specifically, the controller 140 may be programmed to receiving information describing an amount of a requested individual dose, sending instructions to the cyclotron to produce the individual quantity of the radioactive water 50, and send instructions to the dispensing unit 54 to dispense the individual quantity of the radiopharmaceutical 56 requested by the operator.

Described herein is a standalone radiopharmaceutical preparation apparatus, also referred to herein as an integrated hotcell, a system that includes the integrated hotcell, and a method of operating the integrated hotcell. In various embodiments, the apparatus and systems described herein provide a PET/SPECT chemistry synthesis platform for production and development of new tracers. The integrated preparation apparatus may have a reduce cost to enable the apparatus to be utilized in emerging market hospitals, regional hospitals and academic sites that require a low cost, easy to site and simple to operate and service local PET tracer production center.

The integrated hotcell has a relatively small footprint to enable the hotcell to be installed in a plurality of locations having limited space, such as for example, within a room containing the medical imaging system. The integrated hotcell meets or exceeds ISO and GMP standards for the preparation and delivery of a radiopharmaceutical suitable for injection into a patient. The integrated hotcell includes a compartment that functions as a clean room like environment and as a result the compartment is configured to meet or exceed ISO 7 standards. The clean room like environment is outfitted to include both a synthesis module and a closed aseptic dispensing system, thus eliminating the need of a separate clean room.

In operation, the clean room like environment is operated at a positive pressured compared to the compartments surrounding the clean room like environment. Thus, a quantity of contaminants that may be introduced into the clean room like environment during operation are reduced and/or eliminated. More specifically, the compartments surrounding the clean room like environment may be operated at a negative pressure to both the ISO 7 compartment, e.g. the clean room like environment, and the external environment such that air from the integrated hotcell leaks into the lower pressure area. Similarly air from the compartment surrounding the clean room like environment will leak into lower pressure areas for radioprotection purposes.

In compliance with pharmaceutical manufacture requirements the finished radiopharmaceutical dosage is tested in its primary packaging, i.e. the capped vial using quality control equipment that is also installed in the integrated hotcell. The tested vials may then be removed from the integrated hotcell via a vial out compartment which provides user access to the tested vials or radiopharmaceutical. The integrated hotcell may be installed in a room of low environmental classification, such as ISO 1 or ISO 2, for example, because the integrated hotcell is substantially leak free and operates with a relatively high airflow throughput through HEPA filters and abatement filters.

Access to the integrated hotcell may be achieved via a transfer hatch, such as the door 40, to enable rapid clean-up to the same environmental particulate requirements as the integrated hotcell so that the integrated hotcell environment is protected. The integrated hotcell includes a plurality of intercompartment doors that function as airlocks. The intercompartment doors may be installed between the various compartments installed within the integrated hotcell. Additionally, integrated hotcell includes a plurality of external doors that function as airlocks. The external doors may be installed to enable a user external access to each individual compartment within the integrated hotcell.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

What is claimed is:

1. A standalone radiopharmaceutical preparation hotcell for preparing a radiopharmaceutical, said hotcell comprising:
   a housing;
   a plurality of compartments enclosed within the housing, the plurality of compartments including at least a pharmaceutical synthesizing and dispensing compartment and a different second compartment, the housing separating the plurality of compartments from an external environment where a user of the hotcell is positioned during operation of the hotcell, wherein an interior wall is positioned between the synthesizing and dispensing compartment and the second compartment, the interior wall having an intercompartment door or hatch;
   a compartment pressurization system configured to maintain the synthesizing and dispensing compartment at a first pressure and maintain the second compartment at a different second pressure, wherein the first pressure is greater than the second pressure such that air flows from the synthesizing and dispensing compartment to the second compartment when the intercompartment door or hatch is opened, the compartment pressurization system including a ducting system; and
   a first sensor configured to determine a current pressure of the synthesizing and dispensing compartment and a second sensor configured to determine a current pressure of the second compartment;
   a controller configured to operate at least one of a valve of the compartment pressurization system or a fan of the compartment pressurization system, based on the current pressures, to maintain the synthesizing and dispensing compartment and the second compartment at the first and second pressures.

2. The hotcell of claim 1, wherein the second pressure is a negative pressure relative to the external environment.

3. The hotcell of claim 1, wherein the compartment pressurization system is configured to maintain the synthesizing and dispensing compartment at a clean room like environment that satisfies International Organization for Standardization (ISO) 7 standards.

4. The hotcell of claim 1, wherein the plurality of compartments includes a third compartment enclosed within the housing and the hotcell further comprises second and third external doors or hatches that allow access to the second and third compartments, respectively, from the external environment, the second pressure being a negative pressure relative to the external environment, the compartment pressurization system configured to maintain the third compartment at a negative pressure relative to the external environment.

5. The hotcell of claim 1, wherein the interior wall is shared by the synthesizing and dispensing compartment and the second compartment, the synthesizing and dispensing compartment and the second compartment being sized and shaped such that respective spaces of the synthesizing and dispensing compartment and the second compartment may receive, at most, arms of the user during operation of the hotcell.

6. The hotcell of claim 1, further comprising an external door or hatch that provides access to the second compartment from the external environment.

7. The hotcell of claim 1, further comprising a radiation shield that encapsulates the synthesizing and dispensing compartment.

8. The hotcell of claim 4, wherein the third compartment is accessible from the synthesizing and dispensing compartment.

9. The hotcell of claim 8, wherein the compartment pressurization system is configured to maintain the third compartment at a negative pressure relative to the synthesizing and dispensing compartment.

10. The hotcell of claim 1, wherein the compartment pressurization system includes the fan and the valve, the compartment pressurization system including at least one other valve and at least one other fan.

11. The hotcell of claim 1, wherein the first pressure is a positive pressure relative to the external environment.

12. The hotcell of claim 1, wherein the controller includes a processor configured to execute stored instructions to maintain the first and second pressures.

13. A radiopharmaceutical manufacturing system comprising:
    an integrated hotcell including a housing that surrounds and defines an interior volume, the interior volume including a first compartment and a second compartment, the housing separating the interior volume from an exterior where a user of the hotcell is positioned as the user controls objects in the first compartment and the second compartment, wherein an interior wall is positioned between the first and second compartments, the interior wall having an intercompartment door or hatch;
    a compartment pressurization system configured to pressurize the first and second compartments;
    a first sensor configured to determine a current pressure of the first compartment and a second sensor configured to determine a current pressure of the second compartment; and
    a controller coupled to the integrated hotcell and the compartment pressurization system, the controller configured to operate at least one of a valve of the compartment pressurization system or a fan of the compartment pressurization system, based on the current pressures, to maintain the first and second compartments at first and second pressures, respectively, wherein the first pressure is greater than the second pressure such that air flows from the first compartment to the second compartment when the intercompartment door or hatch is opened.

14. The radiopharmaceutical manufacturing system of claim 13, wherein the interior volume further comprises a third compartment, wherein the first and second pressures are positive and negative, respectively, relative to the exterior, the compartment pressurization system configured to maintain the third compartment at a negative pressure relative to the exterior.

15. The radiopharmaceutical manufacturing system of claim 13, wherein the interior volume further comprises a third compartment and the manufacturing system further comprises second and third external doors or hatches that allow access to the second and third compartments, respectively, from the exterior, the compartment pressurization system configured to maintain the third compartment at a negative pressure relative to the exterior, the third compartment being accessible from the first compartment.

16. The radiopharmaceutical manufacturing system of claim 13, further comprising a radiation shield that encapsulates the first compartment.

17. The radiopharmaceutical manufacturing system of claim 13, wherein the second pressure is a negative pressure relative to the exterior.

18. A method of preparing a radiopharmaceutical using a standalone radiopharmaceutical preparation apparatus, the apparatus including a housing having a plurality of compartments enclosed therein and a compartment pressurization system, the plurality of compartments including at least a first compartment and a different second compartment, the housing separating the plurality of compartments from an external environment where a user of a hotcell is positioned during operation of the hotcell, wherein an interior wall is positioned between the first compartment and the second compartment, the apparatus also including first and second sensors for determining current pressures in the first and second compartments, respectively, said method comprising:

receiving, at a controller, respective inputs based upon the current pressures within the first and second compartments;

controlling, based upon the current pressures, at least one of a valve of the compartment pressurization system or a fan of the compartment pressurization system to maintain the first compartment at a first pressure and the second compartment at a different second pressure, wherein the first pressure is greater than the second pressure;

moving material from the second compartment into the first compartment, wherein a pressure differential between the first and second compartments causes air to flow into the second compartment as the material is moved into the first compartment;

receiving a batch of radioactive water into the first compartment;

generating a batch of radiopharmaceutical from the radioactive water within the first compartment; and subdividing the batch of radiopharmaceutical into individual doses within the first compartment.

19. The method of claim 18, further comprising transferring the radiopharmaceutical to a third compartment that is also enclosed within the housing of the apparatus, third compartment being maintained at a negative pressure relative to the external environment and the first compartment.

20. The method of claim 18, further comprising performing a quality control procedure on the batch of radiopharmaceutical within a third compartment that is also enclosed within the housing.

* * * * *